United States Patent [19]

Kamei et al.

[11] Patent Number: 5,309,222
[45] Date of Patent: May 3, 1994

[54] SURFACE UNDULATION INSPECTION APPARATUS

[75] Inventors: Mitsuhito Kamei; Mikio Tachibana, both of Hyogo, Japan

[73] Assignee: Mitsubishi Denki Kabushiki Kaisha, Tokyo, Japan

[21] Appl. No.: 913,059

[22] Filed: Jul. 14, 1992

[30] Foreign Application Priority Data

Jul. 16, 1991 [JP] Japan .................................. 3-175140
Apr. 13, 1992 [JP] Japan .................................. 4-118544

[51] Int. Cl.$^5$ ..................... G01B 11/24; G01B 11/30
[52] U.S. Cl. ..................................... 356/371; 356/376
[58] Field of Search .............................. 356/371, 376

[56] References Cited

U.S. PATENT DOCUMENTS

| | | | |
|---|---|---|---|
| 3,804,521 | 4/1974 | Sprague | 356/371 |
| 4,212,073 | 7/1980 | Balasubramanian | 356/376 |
| 4,215,939 | 8/1980 | Miller et al. | 356/371 |
| 4,794,550 | 12/1988 | Grienkamp, Jr. | 356/376 |
| 5,003,615 | 3/1991 | Sutz | 356/376 |
| 5,024,529 | 6/1991 | Svetkoff et al. | 356/376 |
| 5,102,223 | 4/1992 | Uesugi et al. | 356/376 |

FOREIGN PATENT DOCUMENTS 56-76004  6/1981  Japan .
2-11085   3/1990  Japan .
3-175140  7/1991  Japan .
4-12256   1/1992  Japan .

Primary Examiner—Robert J. Warden
Assistant Examiner—L. M. Crawford
Attorney, Agent, or Firm—Burns, Doane, Swecker & Mathis

[57] ABSTRACT

A surface undulation inspection apparatus for detecting a defect of a fine undulation including a change of a gentle profile or the like on a suitable surface of a specimen to be inspected, wherein a patterning light source is opposed to an image pickup lens having a pin hole with a specimen interposed therebetween to pin-hole image pickup the patterning light source through the specimen to be inspected whereby a ray passing through the specimen to be inspected is specified as a principal ray, and a local surface undulation defect on the surface of the specimen is stressed and a defective part is specified. Further, a display pattern generated by a pattern generator is displayed on a pattern display element to used it as a patterning light source, the pattern generator is feedback controlled by a deviation calculation circuit, a standard data generator circuit, a pattern width coincidence decision circuit and a comparison data circuit, or a coordinate conversion circuit and an angle detector circuit, and an intensity of the display pattern is regularly changed in an analog manner to detect an abnormality on the basis of a differential from the image data.

6 Claims, 11 Drawing Sheets

SURFACE UNDULATION INSPECTION APPARATUS

BACKGROUND OF THE INVENTION

1. Field of the Invention

This invention relates to a surface undulation inspection apparatus which detects an undulatory defect having a small profile change among defects generated in glass, a metal sheet, a coated surface and the like.

2. Description of the Prior Art

The inspection of a surface defect of a sheet material has been conducted by an apparatus for projecting a laser light on a specimen surface to receive a reflecting light, or a system for uniformly illuminating a specimen surface and photographing the specimen surface by a television camera, a line sensor or the like. However, in this apparatus or system, when a surface profile of a defect becomes small, the intensity and change in position of the reflecting light are very small, rendering detection impossible.

On the other hand, as an apparatus for measuring a surface flatness of a surface roughening of a coated surface, there is a "Flatness Measuring Apparatus" disclosed in Japanese Patent Laid Open Publication No. 76,004/1981. FIG. 1 shows the structure of a conventional flatness measuring apparatus disclosed in said patent publication, in which numeral 25 denotes a light source, 26 denotes a lattice pattern, 31 denotes a projection lens, 41 denotes a specimen to be inspected, 27 denotes a focussed lattice pattern image, and 61 denotes a photoelectric conversion element.

The operation of the conventional apparatus will be described below. The lattice pattern 26 illuminated by the light source 25 is projected by the projection lens 31. When the specimen to be inspected 41 is inserted in the midst of a projection channel, the projection channel is bent by the specimen to be inspected 41. The photoelectric conversion element 61 is moved on the lattice pattern image 27 focussed at that time to electrically read the lattice pattern image. In such a structure as just mentioned, when an abnormal flatness such as a distortion occurs in the specimen to be inspected, a distortion occurs in the lattice pattern image 27 being focussed and a pattern pitch changes. This is detected by the photoelectric conversion element 61, which is statistically compared with an average normal pitch to thereby arithmetically calculate a flatness within a view of inspection.

Since the conventional flatness measuring apparatus is constructed as described above, the view of inspection is determined by an installed position of the specimen to be inspected within a pattern projection system and is measured in mm. Because of this, the efficiency for inspecting a surface having a wide area is very poor. In a case of a reduced projection system (in the aforesaid publication, magnification $\beta$ is less than 1), a large aperture projection lens is required in order to widen the view of inspection. For example, in order that a specimen is arranged at a position one half ($\frac{1}{2}$) of a projection distance to realize the view of inspection having a diameter of 50 cm, an aperture of a lens is necessary to have 1 m or more, which is unrealistic. Further, in order that a specimen is arranged at a position one half ($\frac{1}{2}$) of a projection distance in an enlarged projection system to realize the view of inspection having a diameter of 50 cm, the moving scanning distance of the photoelectric element 61 must also be 1 m, and a burden of the mechanism of the system increases in terms of the construction of a system. Moreover, the conventional flatness measuring apparatus has no object to detect an average distortion within a view of field to detect a local distortion. Therefore, the conventional apparatus statistically processes the change of pitch within a view of field, failing to detect a local defect such as a small undulation, most of which occurs in a normal surface. Further, since light passing through a local portion of the specimen surface is not optically specified, an optical abnormality resulting from a small undulation becomes embedded in the reflected light from a major portion of normal surface, possibly rendering detection impossible. Thus, the conventional apparatus has many problems in practical use and principle for the surface inspection.

FIG. 2 is a structural view of a conventional surface undulation inspection apparatus shown, for example, in the specification and drawings attached to Japanese Patent Application No. 175140/1991. In the drawings, numeral 1 denotes a patterning light source for generating a desired light source pattern, and numeral 2 denotes a specimen to be inspected for any undulatory defects. Numeral 3 denotes a camera which is arranged opposite to the patterning light source 1 and which encloses a pin hole to selectively utilize only a principal ray for focussing.

The operation of the above disclosure will be described. The patterning light source 1 is opposed to the camera 3 having a pin hole enclosed therein with the specimen to be inspected 2 sandwiched therebetween, and a focal position of the camera 3 is adjusted to the patterning light source 1 via the specimen to be inspected 2. At that time, the light contributed to the image pickup of the camera 3 is selected in the principal ray alone by the pin hole to form an image of a light source pattern generated by the patterning light source 1. In the image pickup system utilizing only the principal ray, the light contributed to the focussing comprises only a straight line light in which an object is joined with an image surface and which crosses on the pin hole. In the optical conditions in the state as described, the behavior of a fine straight line beam from the camera 3 to the patterning light source 1 may be taken into consideration. When a fine rugged portion such as an undulation occurs on the specimen to be inspected 2, a slight inclination of the specimen surface resulting from the rugged portion is amplified by an optical lever effect of a light beam, and finally, a distortion occurs in an image-picked up light source pattern. Accordingly, a change from a regular pattern as described above is detected to enable inspection of a surface undulation of the specimen to be inspected 2.

The conventional undulation inspection apparatus is constructed as described above. The inspection capacity depends upon the shape of the light source pattern of the patterning light source 1. However, since the optimum light source pattern is decided as a result of repeated experiments, it is difficult to proceed with; 1 the standardization of hardware for the inspection apparatus and the lower price resulting therefrom. Further, since the inspection principle assumes a plane, if a three-dimensional surface applied with a design of automobiles, home electric appliances or the like, for example, is taken up as an object to be inspected, a deviation of an image pickup pattern occurs at the outset in a normal surface, rendering detection of undulation impossible.

Moreover, in the actual detection of an undulation defect, a system for deciding an optimum pattern pitch with respect to a limit sample is not determined so that it is necessary to repeat "trial and error" many times and the efficiency for preparation of apparatus is very poor. Further, in a case where a flaw resulting, for example, from rolling, grinding or cutting remains on the surface of a specimen to be inspected, visibility of an image pickup pattern is extremely lowered dependent on the setting direction of the light source pattern, sometimes rendering inspection impossible. Furthermore, in a case where an undulation defect to be detected is extremely small, when a pitch of a light source pattern is made to be smaller than a predetermined level, an electronic moire phenomenon occurs to render inspection impossible.

SUMMARY OF THE INVENTION

This invention has been accomplished in order to overcome the problems as noted above. An object of this invention is to provide a practical surface undulation inspection apparatus which can freely select the field of vision of inspection, which requires no movement of a photoelectric element and which can detect a fine undulation within the field of vision.

A further object of this invention is to provide a surface undulation inspection apparatus which enables inspection of a fine undulation on a surface of a suitable object at a practical level.

According to a first aspect of the invention, a patterning light source is arranged opposite to a pin hole with a specimen to be inspected sandwiched therebetween so as to pickup an image of the patterning light source via the pin hole.

In the surface undulation inspection apparatus according to the first aspect of the invention, the patterning light source is subjected to the pin hole image-picking up through the specimen to be inspected. As a result, the light passing through the specimen to be inspected can be specified as an optical principal ray. An optical lever effect can be generated. The corresponding light indicates an abnormality with respect to a local surface undulation on the surface of the specimen, and a defect can be stressed and a defective portion can be specified. For detection of a pattern in the inspection apparatus according to this invention, a camera element such as normal CCD is utilized, and a movement of a photoelectric element is not necessary.

According to a second aspect of the present invention, an image pickup lens for focussing a patterning light source through a specimen to be inspected is disposed between the specimen to be inspected and a pin hole, said pin hole being arranged to select only a principal ray among rays of light passing through said image pickup lens.

In the surface undulation inspection apparatus according to the second aspect of the invention, since the image pickup lens is provided, an undulation can be detected even if the patterning light source has no sufficient brightness and even if the reflectance of the surface of a specimen to be inspected is low. Further, the field of vision of inspection can be suitably set as an image pickup field of vision of a lens if the size of the patterning light source is large enough.

According to a third aspect of the invention, the apparatus comprises a pattern generator for generating a display pattern displayed on a pattern display element forming a pattern light source, a driver for driving the pattern display element of the display pattern, and a synchronous signal generator for synchronizing the driver with scanning of a camera.

In the pattern display element in the surface undulation inspection apparatus according to the third aspect of the invention, a suitable optimum light source pattern is generated according to a display pattern generated by a pattern generator to realize a surface undulation inspection apparatus which enables standardization of a light source hardware.

According to a fourth aspect of the invention, there are provided a deviation calculation circuit wherein a stripe-like display pattern is generated in a pattern generator, the number of stripes of an image data from a camera are counted, and a deviation with respect to a width data of the set stripe pattern is calculated, and a standard data generation circuit wherein the width data of the stripe pattern corresponding to the counted value of the number of stripe from the deviation calculation circuit is fed back to the deviation calculation circuit, whereby the display pattern generated by the pattern generator is changed so that a deviation from the deviation calculation circuit is zero.

In the pattern generator in the surface undulation inspection apparatus according to the fourth aspect of the invention, the display pattern to be generated is changed so that a deviation of the width data of the stripe pattern from the standard data generation circuit calculated by the deviation calculation circuit is zero to thereby enable removal of influence of a three-dimensional shape.

According to a fifth aspect of the invention, there are provided a comparison data circuit wherein a stripe-like pattern is generated in a pattern generator to produce a pattern width data corresponding to said display pattern, and a pattern width coincidence decision circuit for the comparison of coincidence between a stripe pattern width data of an image data from a camera and a pattern width data from the comparison data circuit, whereby the number of stripes of the display pattern generated by the pattern generator is increased till the result of decision of the pattern width coincidence decision circuit indicates inconsistency to cause a stripe pitch to be reduced.

The pattern generator in the surface undulation inspection apparatus according to the fifth aspect of the invention enables the decision of the optimum lattice condition with respect to a limit defect by causing the number of stripes of the display pattern generated and the stripe pitch to be reduced till the result of coincidence comparison between the pattern width data from the comparison data circuit and the stripe pattern width data of the image data from a camera carried out in the pattern width coincidence decision circuit indicates inconsistency.

According to a sixth aspect of the invention, there are provided a coordinate conversion circuit wherein a radial pattern is first generated by a pattern generator, and an image data from a camera is developed in polar coordinates from a center of an image, and an angle detection circuit for detecting an angle at which the polar coordinate data indicates the largest amplitude, whereby a lattice stripe-like display pattern parallel with the angular direction at which the polar coordinate data detected by the angle detection circuit indicates the largest amplitude is generated later by the pattern generator.

The pattern generator in the surface undulation inspection apparatus according to the sixth aspect of the invention enables the decision of the optimum lattice direction of the display pattern with respect to a surface having a suitable worked flaw by first generating the radial pattern and thereafter generating the lattice stripe-like display pattern parallel with the angular direction at the polar coordinate data developed in polar coordinate in the coordinate conversion circuit detected by the angle detection circuit.

According to a seventh aspect of the invention, there is provided an analog differential circuit for generating a display pattern indicative of a regular change of intensity in an analog manner by a pattern generator and calculating a differential between an image data from a camera and an output waveform of the pattern generator to detect an abnormality.

The analog differential circuit in the surface undulation inspection apparatus according to the seventh aspect of this invention enables the detection of an extremely small undulation by calculating a differential between a display pattern indicative of a regular change of intensity in an analog manner generated by the pattern generator and an image data from a camera which photographed said display pattern to detect an abnormality.

The aforesaid and other objects and new features will be more completely apparent from reading the ensuing detailed description in conjunction with the accompanying drawings. It is to be noted however that the drawings are merely for explanation and the scope of this invention is not limited thereby.

DETAILED DESCRIPTION OF THE PREFERRED EMBODIMENTS

Preferred embodiments of this invention will be described hereinbelow with reference to the drawings.

Embodiment 1

Figure 3:
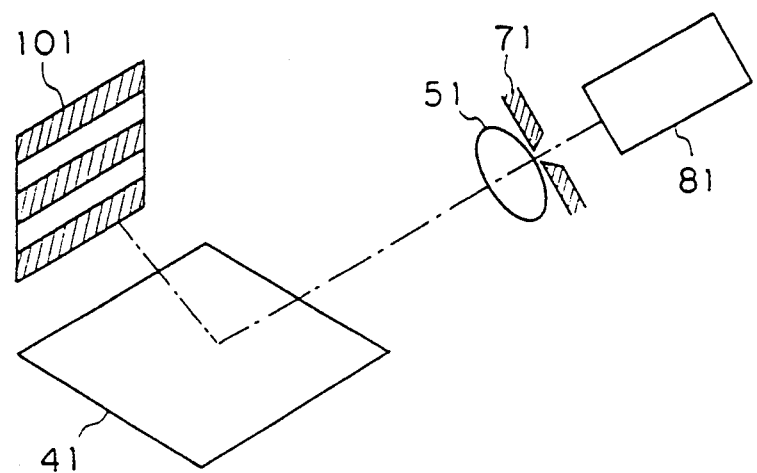
FIG. 3 is a structural view showing a basic optical system of a surface undulation inspection apparatus according to a first embodiment of this invention.
Figure 4:
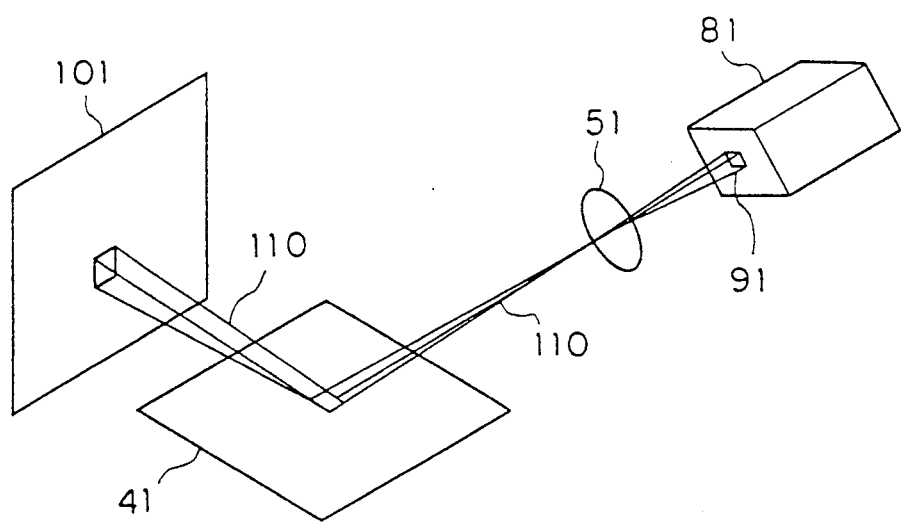
FIG. 4. is an explanatory view of inspection conditions according to the first embodiment of this invention.
Figure 5:
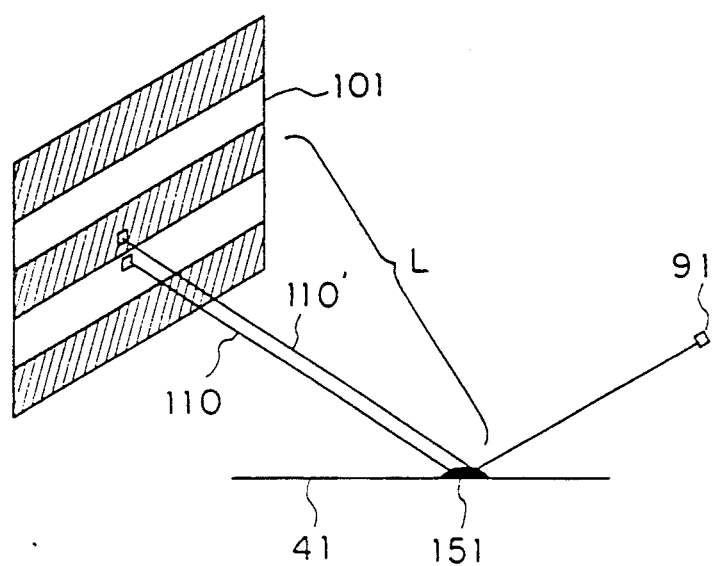
FIG. 5 is an explanatory view of the actual inspecting operation of the first embodiment according to this invention.
Figure 6:
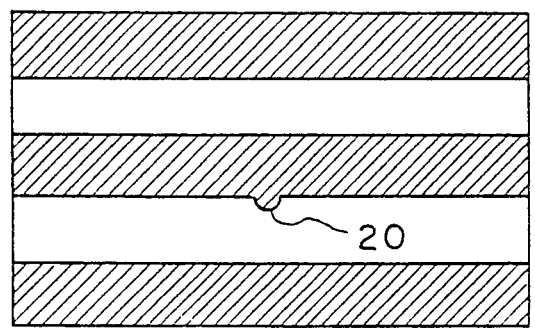
FIG. 6 is a schematic plan view showing an example of image as one example of the inspection result according to the first embodiment of this invention.

FIG. 3 is a structural view showing a basic optical system of a surface undulation inspection apparatus according to a first embodiment of this invention. In FIG. 3, reference numeral 101 denotes a patterning light source, 41 denotes a specimen to be inspected, 51 denotes an image pickup lens, 71 denotes a pin hole, and 81 denotes a camera. FIG. 4 is an explanatory view for explaining the inspection conditions, FIG. 5 is an explanatory view for explaining the actual inspecting operation, and FIG. 6 is a schematic plan view showing an example of an image as one example of the inspection result.

The operation of the apparatus will be described below. The patterning light source 101 is arranged opposite to the image pickup lens 51 with the specimen to be inspected 41 sandwiched therebetween, and a focal position of the image pickup lens 51 is adjusted with respect to the patterning light source 101 via the specimen to be inspected 41. The image pickup light passing through the lens selects only a principal ray by the pin hole provided on the optical axis to form an image of the patterning light source on the camera 81. In the image pickup system which selects only the principal ray, the light contributed to focussing is a mere straight line light by which an object and an image surface are joined and which crosses on the pin hole. The optical conditions in such a state as described can be analyzed by a model shown in FIG. 4. In FIG. 4, reference numeral 101 denotes a patterning light source, 41 denotes a specimen to be inspected, 51 denotes an image pickup lens, 81 denotes a camera, 91 denotes one element within a camera element, and 110 denotes a beam in which the element 91 is reversedly projected on the side of the patterning light source 101. That is, as the optical conditions, the behavior of the fine straight line beam 110 in which one element within an array element 91 shown in FIG. 4 is reversely projected on the side of the patterning light source 101 may be taken into consideration. In other words, information detected by the element 91 is information on the light path of the beam 110, which will be information at a specific position on the specimen in the case where the specimen to be inspected is normal. In the whole camera 81 with these elements integrated, a group of beams in which the elements of the camera 81 are reversely projected to the specimen to be inspected 41 can be assumed, and accordingly, the whole surface 41 of the specimen to be inspected can be inspected.

The actual inspecting operation will be described with reference to FIG. 5. In FIG. 5, the element 91 is joined with the white side of a white and black boundary area on the patterning light source 101 via the specimen to be inspected 41 in the light path 110. At that time, when an undulation 151 occurs on the specimen to be inspected 41 and an illumination point of the beam 110 is inclined, the beam 110 is also inclined as at 110'. The inspection capacity of undulation depends on to what extent the beam 110' is deviated from the original beam 110. Since such an inspection principle is considered by a beam-like ray of light, the light lever effect can be utilized. To what point on the patterning light source 101 the joined point of the beam 110' is moved is decided by amplifying the inclination of the undulation 151 by the distance between the patterning light source 101 and the specimen to be inspected 41. By setting the distance, the detection sensitivity of the inclination of undulation can be suitably increased or decreased. Accordingly, by setting a suitable distance L, the joined point of the beam 110' on the patterning light source 101 is on the black side of the white and black boundary area, and as a result, an output of the element 91 is changed from an output corresponding to white of a pattern to an output corresponding to black by the occurrence of the undulation 151. At this time, other elements of the camera 81 indicate no change since a change in the surface of the specimen on the corresponding beam is not present. As the result, in a video signal outputted from the camera 81, a deformation from a regular pattern occurs at a position corresponding to the element 91 as shown at a projection 20 of FIG. 6. Accordingly, the presence of an undulation can be detected by detecting a change from the regular pattern. As will be apparent from the above explanation, the field of vision of inspection of the inspection apparatus according to this invention is decided as the effective field of vision of the image pickup lens 5, and at this time, if the size of the patterning light source is set so that the effective field of vision can be covered, it can be suitably set by the selection of the focal length of the lens. The signal processing for detecting a change from the regular pattern can be done by use of commercially available various image processing techniques. Various modes for carrying out the inspection apparatus according to the applied contents of these signal processing techniques are not beyond the scope of the patent according to this invention.

In the inspection apparatus according to this embodiment, the selection performance of the principal ray according to the pin hole is important. As an experimental example, assuming that the focal length of lens is 55 mm, and an object to be inspected is a fine undulation whose height is 0.5 $\mu$m, and the stretched aperture of the skirt is 0.5 mm, a diameter of a pin hole for limit of detection is 2.5 mm. The detection of the undulation was impossible with a diameter of a pin hole which is larger than that of the above. In a case of a diameter of a pin hole less than 1 mm, stable inspection can be made without being affected by disturbance light.

Embodiment 2

In the aforementioned Embodiment 1, the image picking-up was made on the premise that a lens is used. It was confirmed however that a brightness of a patterning light source is increased and a pin hole having an aperture of 0.2 mm is used, whereby a sufficient resolution of inspection can be provided and a lens can be omitted. As the result, in a case where a patterning light source can be set to a high brightness or in a case where a reflectance of the surface of a specimen is high, similar effect can be obtained by a practical image pickup system which uses only a pin hole omitting an image pickup lens.

Embodiment 3

Figure 1:
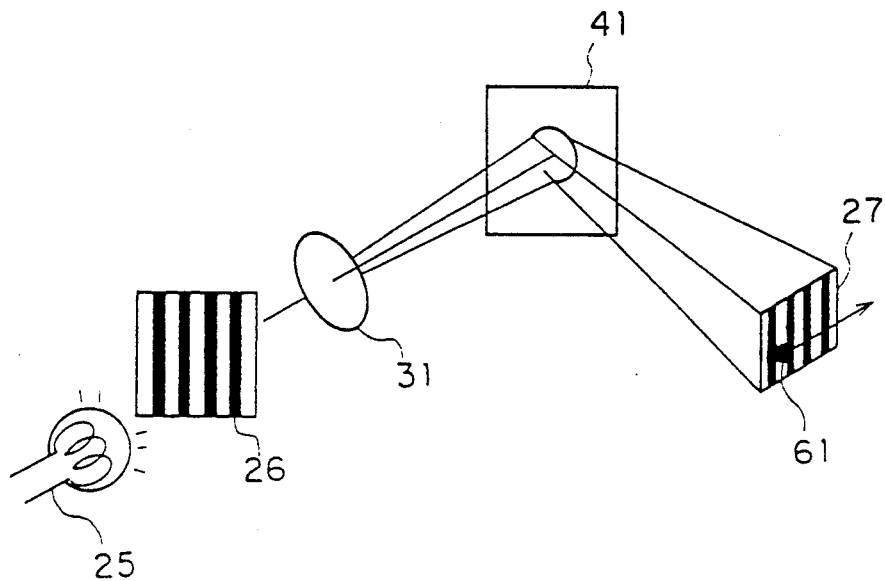
FIG. 1 is a structural view showing a conventional flatness inspection apparatus.
Figure 2:
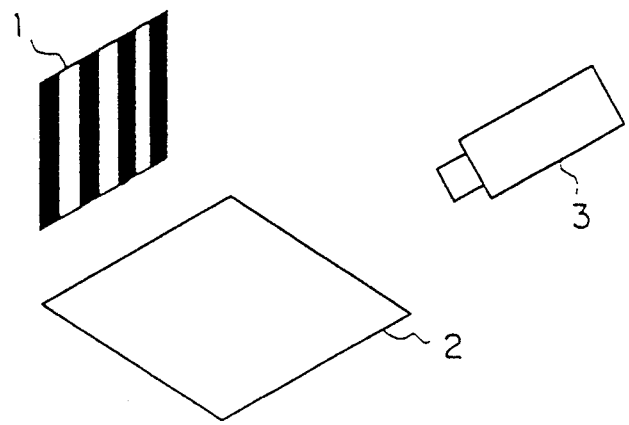
FIG. 2 is a structural view showing a conventional undulation inspection apparatus.
Figure 7:
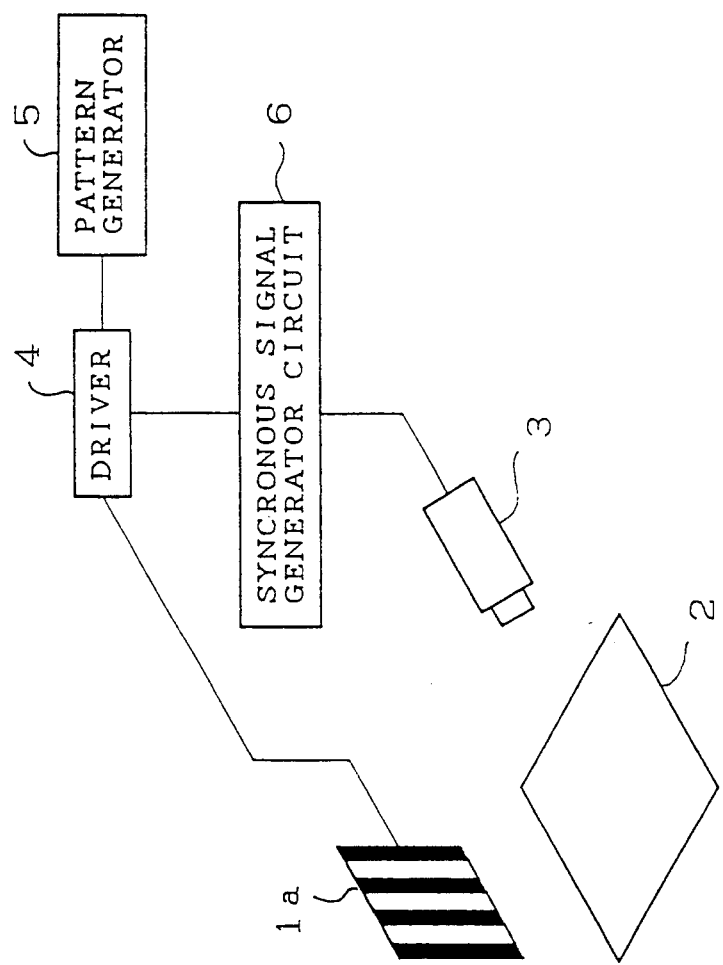
FIG. 7 is a structural view showing a surface undulation inspection apparatus according to a third embodiment of this invention.

FIG. 7 is a structural view showing a surface undulation inspection apparatus according to Embodiment 3 of this invention. In FIG. 7, reference numerals 2 and 3 denote a specimen to be inspected and a camera, respectively, which are the same as those shown in FIG. 2. Numeral 1a denotes a pattern display element used as the patterning light source 1 shown in FIG. 2, and 4 denotes a driver for driving the pattern display element 1a. Numeral 5 denotes a pattern generator which generates a display pattern displayed on the pattern display element 1a to supply it to the driver 4, and 6 denotes a synchronous signal generator circuit for synchronizing the driver 4 with scanning of the camera 3.

Embodiment 4

Figure 8:
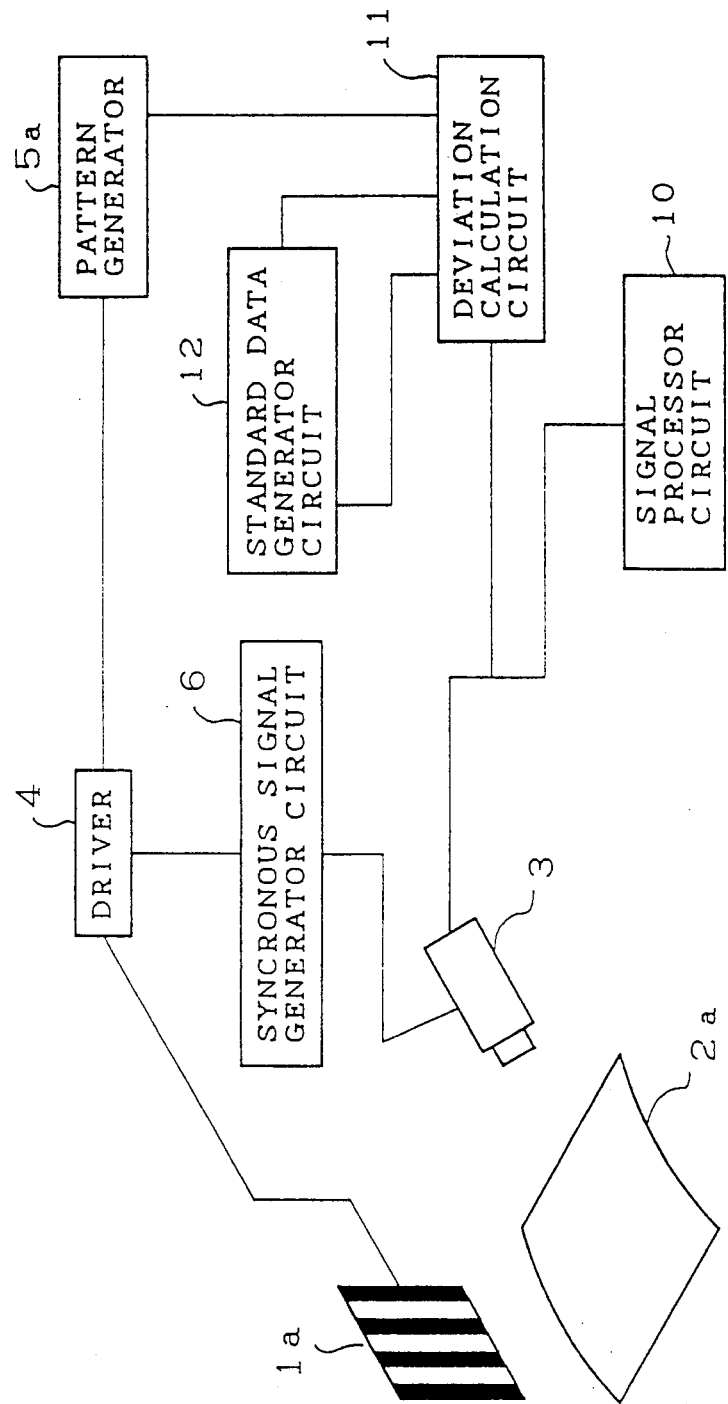
FIG. 8 is a structural view showing a surface undulation inspection apparatus according to a fourth embodiment of this invention.

Next, Embodiment 4 of this invention will be described. FIG. 8 is a structural view showing a surface undulation inspection apparatus which can inspect a surface undulation of a three-dimensional shaped object, in which the same reference numerals are attached to the same parts as those of FIG. 7 and a description thereof is omitted. Numeral 2a denotes a specimen to be inspected having a three-dimensional shape, and numeral 10 denotes a signal processor circuit for extracting an undulation defect of the specimen to be inspected 2a from final image data taken from a camera. Numeral 11 denotes a deviation calculation circuit for arithmetically outputting a deviation with respect to a set stripe pattern width data, and 12 denotes a standard data generator circuit for producing a corresponding stripe pattern width data on the basis of a counted value outputted from the deviation calculation circuit 11 to feed back it to the deviation calculation circuit 11. Numeral 5a denotes a pattern generator different from that indicated at numeral 5 in FIG. 7 in that a stripe-like display pattern is generated and a display pattern generated is changed so that a deviation outputted by the deviation calculation circuit 11 is zero.

Figure 9:
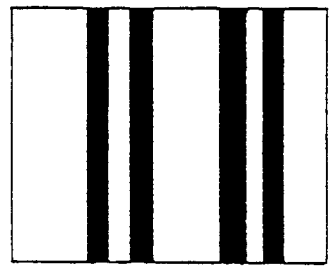
FIG. 9 is an explanatory view showing an initial image taken by a camera in the aforementioned embodiment.
Figure 10:
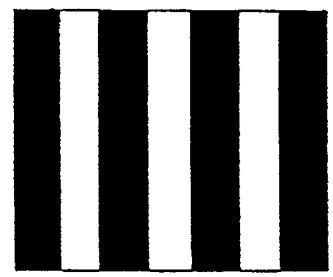
FIG. 10 is an explanatory view showing a final image feed-back corrected in the aforementioned embodiment.

The operation of the apparatus will be described below. FIG. 9 and FIG. 10 are explanatory views showing one example of an initial image picked up by the camera 3 and one example of a final image feed-back corrected, respectively. In the surface undulation inspection apparatus of Embodiment 3 shown in FIG. 7, the specimen to be inspected was assumed to be flat and if an irregularity is considered in an image pickup pattern, it has been specified that such irregularity results from an undulation. However, surfaces of vehicles, home electric appliances or the like which are important in design are less in such a flat portion but the normal surface of the specimen to be inspected 2a is a three-dimensional shaped surface already accompanied with a rugged portion as shown in FIG. 8. When an undulation inspection utilizing a principal light with a lattice having equal pitches depicted on a pattern display element is applied to the surface as described, the result is as shown in FIG. 9.

The operation of the apparatus shown in FIG. 7 will be described below. The pattern display element 1a is opposed to the camera 3 with the specimen to be inspected 2 sandwiched therebetween, and the focal position of the camera 3 is adjusted to the pattern display element 1a via the specimen to be inspected 2. At that time, as the light contributed to the image picking-up of the camera 3, only the principal light is selected by the pin hole provided on the optical axis to form an image of a light source pattern generated by the pattern display element 1a. When the pattern generator 5 generates a regular lattice-like space pattern signal, for example, a lattice stripe is generated in the pattern display element 1a via the driver 4. Since the driver 4 and the camera 3 are forcibly synchronized by the synchronous signal generator 6, the camera 3 can pick up the lattice stripe on the pattern display element 1a in a stable manner. The optical condition in such a state is the same as the basic principle for detection of an undulatory defect whose surface profile is small by way of the conventional surface undulation inspection apparatus shown in FIG. 2. That is, as the image pickup system which selects only the principal ray, the light contributed to the focussing is limited to only the straight line light by which an object and an image surface are joined and which crosses on the pin hole, and the light lever effect can be picked up as a deviation of a light source pattern. In addition, the shape of a light source pattern generated by the pattern display element 1a can be suitably generated by the pattern generator 5, and standardization of the hardware of a surface undulation inspection apparatus becomes possible. As the pattern display element 1a, all commercially available general-use display elements such as normal CRT, liquid crystal display panel, liquid crystal projector, TV monitor, LED display panel, etc. can be utilized. It is to be noted that various modes for carrying out inspection apparatus such as changes in kind of these display elements and changes in a driving system resulting therefrom are not beyond the scope of claims according to the present invention.

With a three-dimensional specimen to be inspected which has surface undulations, a lattice image is irregularly observed at the outset, and detection of a delicate undulation becomes difficult. Thus, the apparatus of FIG. 8 must first be experimentally verified or calibrated. Accordingly, first, a specimen which has only a normal three-dimensional shape and has no fine undulation defect is prepared, and the deviation calculation circuit 11 receives a signal from the camera to count the number of stripes within an image. The counted result is outputted to the standard data generator 12. The standard data generator 12 feeds back the standard stripe pattern width data corresponding to the number of stripes to the deviation calculation circuit 11 from the counted result of the number of stripes from the deviation calculation circuit 11. The deviation calculation circuit 11 calculates a deviation between the standard stripe pattern width data, the image pickup stripe data inputted from the camera 3 and the pattern width data to output deviation information to the pattern generator 5a. The pattern generator 5a feed-back controls the pitches, stripe widths or the like of the display pattern so that the deviation is zero on the basis of the deviation information from the deviation calculation circuit 11. In this experimental verification of function, the pattern picked up by the camera 3 and obtained after three to four times of feed back correction has equal pitch and equal stripe width as shown in FIG. 10. Thereafter, the specimen is replaced by an actual object to be inspected, whereby the signal processor 10 can detect undulations regardless of the three-dimensional shape of the specimen.

Embodiment 5

Figure 11:
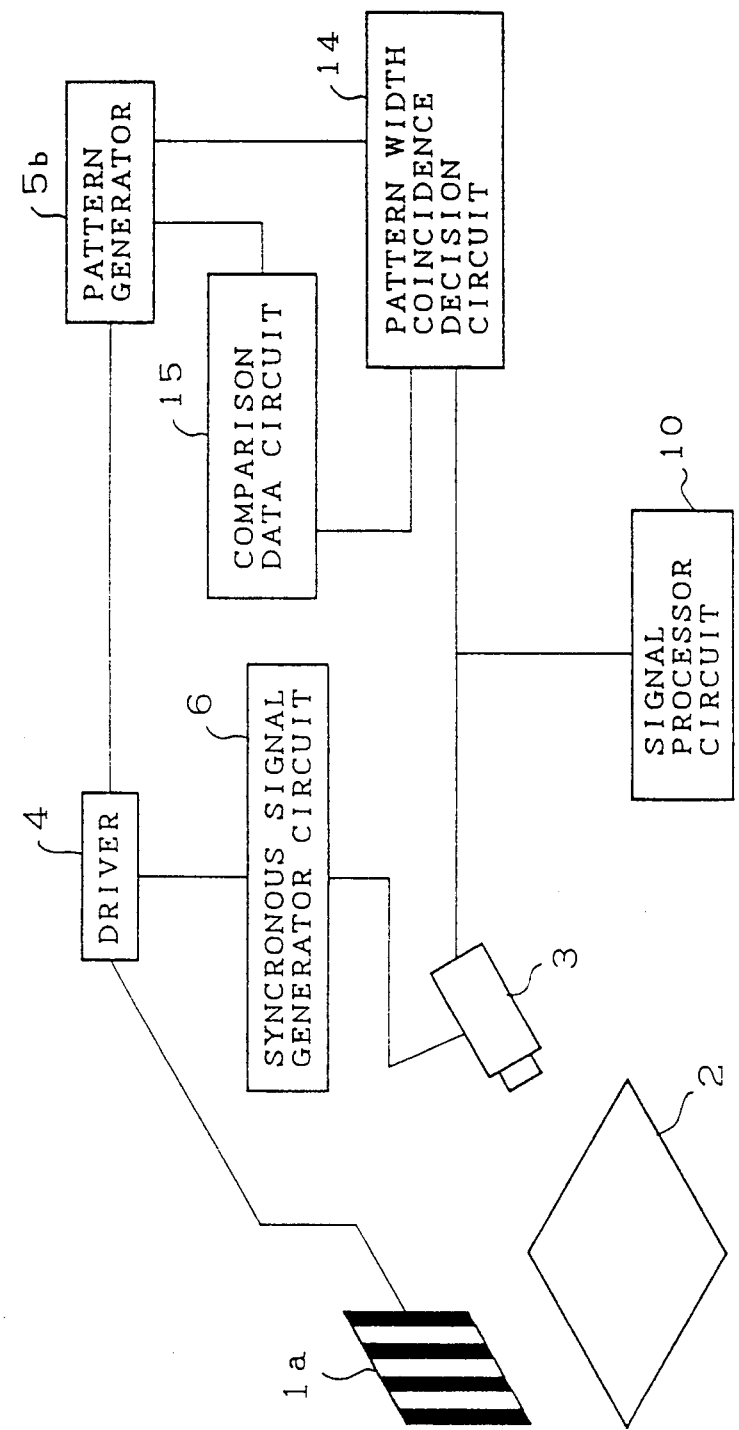
FIG. 11 is a structural view showing a surface undulation inspection apparatus according to a fifth embodiment of this invention.

Embodiment 5 of this invention will be described below with reference to the drawings. FIG. 11 shows a surface undulation inspection apparatus in which a limit defect sample has an optimum light source pattern. In FIG. 11, the same parts as those shown in FIGS. 7 and 8 are indicated by the same reference numerals. In FIG. 11, reference numeral 14 denotes a pattern width coincidence decision circuit for receiving a signal from the camera 3 to make a comparison of the coincidence between a stripe pattern width data within an image and a set stripe pattern width data and outputting the result obtained therefrom. The numeral 15 denotes a comparison data circuit for producing pattern width data corresponding to a display pattern generated by a pattern generator 5b (later described) to output it to the pattern width coincidence decision circuit 14. Numeral 5b denotes a pattern generator different from that indicated by numerals 5 and 5a in FIGS. 7 and 8, respectively, in that it has a function of changing the display pattern for carrying out an increase in the number of stripes of a display pattern generated and reduction in stripe pitch until the decision result of the pattern width coincidence decision circuit 14 indicates inconsistency.

The operation of the apparatus will be described below. In the surface undulation inspection apparatus utilizing the optical lever effect from the principal ray, a pattern display element 1a as a patterning light source and a camera 3 for selectively focussing only a principal ray are arranged on one side and the other side, respectively, through a specimen to be inspected 2, whereby an undulation is detected from a deviation of a lattice pattern picked up the camera 3. At that time, the conditions of the number of stripes, pitches or the like of the lattice pattern are directly connected to the detection capacity to the extent an undulation is detected. Practically, it is necessary to determine the lattice conditions with respect to the given state of specimen surface and the limit defective sample. First, an image of a principal ray is picked up by the camera with respect to the limit defective sample under the suitable conditions. A signal from the camera 3 is inputted into the pattern width coincidence decision circuit 14. On the other hand, the pattern generator 5b outputs the lattice condition being now displayed to the comparison data circuit 15, and the comparison data circuit 15 inputs the comparison data corresponding to the display pattern into the pattern width coincidence decision circuit 14. As a result, the pattern width coincidence decision circuit 14 compares the pattern data with the comparison data. At that time, if both the patterns are in coincidence, a limit undulation defect cannot be detected, and a coincidence signal is sent to the pattern generator 5b. In the pattern generator 5b, the surface lattice condition is changed to an increase in the number of stripes and the direction of reducing the stripe pitch. Such a feedback control is continued until the pattern width coincidence circuit 14 outputs an inconsistency signal to decide the final display lattice condition with respect to the limit defect sample. After the final display lattice condition has been decided, the lattice condition is fixed, and inspection can be made by the signal processor 10. It is to be noted needless to say that when the pattern width coincidence decision circuit 14 issues an inconsistency signal in the first setting pattern, a feedback control is applied in a direction of changing the lattice condition to the direction of reduction in the number of stripes and of enlargement of stripe pitch, and various modes for carrying out the inspection apparatus caused by a difference in the lattice condition and the directivity of the way of applying the feedback with respect thereto, that is, the way of combining the lattice conditions is not beyond the scope of claims according to the present invention.

Embodiment 6

Figure 12:
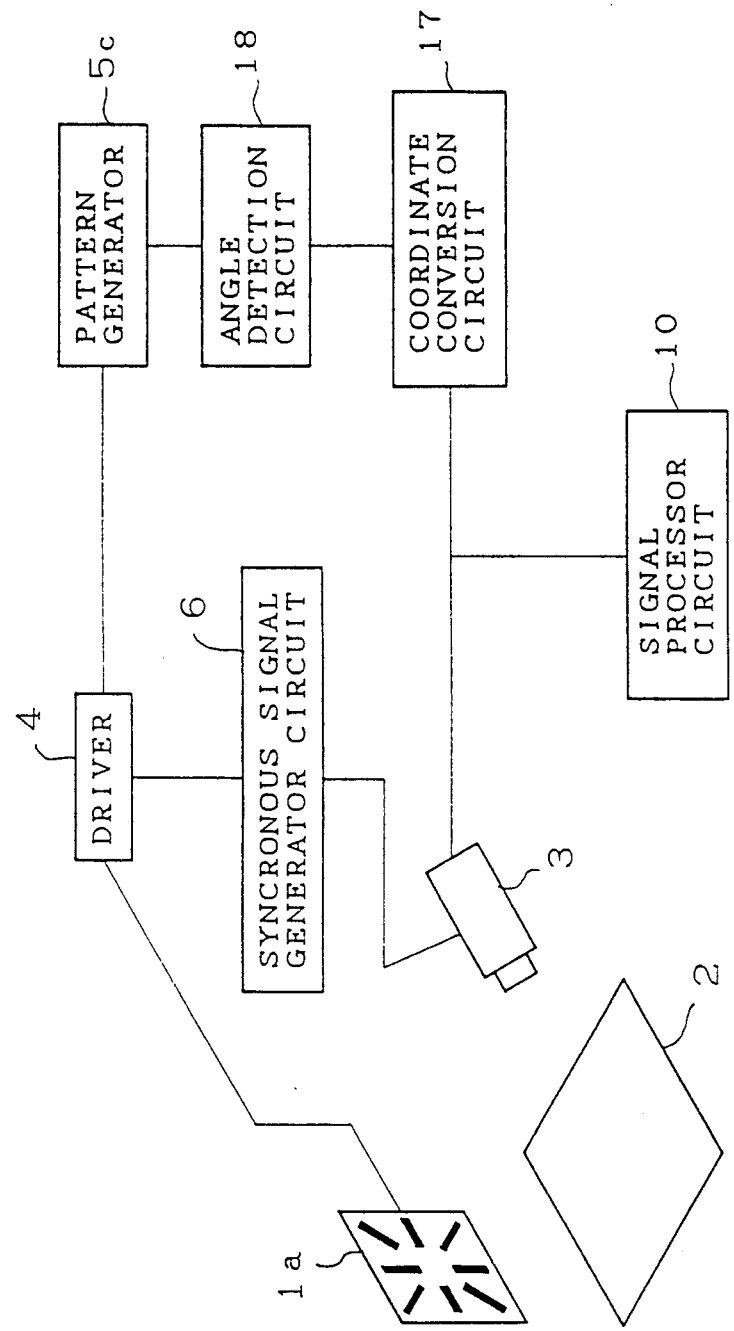
FIG. 12 is a structural view showing a surface undulation inspection apparatus according to a sixth embodiment of this invention.

Next, Embodiment 6 of this invention will be described below. FIG. 12 is a structural view showing a surface undulation inspection apparatus having a function of automatically deciding, in an optimum direction, a developing direction of a lattice pattern with respect to a specimen to be inspected in which a worked flaw caused by, for example, rolling, grinding, cutting or the like remains on the surface thereof, in which the same parts as those shown in FIG. 11 are indicated by the same numerals. In FIG. 12, numeral 17 denotes a coordinate conversion circuit for subjecting an image data taken from a camera 3 to polar, coordinate development from the center of the image, and numeral 18 denotes an angle detection circuit for detecting an angle at which the polar coordinate data outputted from the coordinate conversion circuit 17 indicates the maximum amplitude. Numeral 5c denotes a pattern generator different from those indicated at 5, 5a and 5b in FIGS. 7, 8 or 11 in that it has a function of generating a lattice stripe-like display pattern parallel with the angular direction at which a polar coordinate data detected by the angle detection circuit 18 indicates the maximum amplitude, after a radial display pattern has been first generated.

Figure 13:
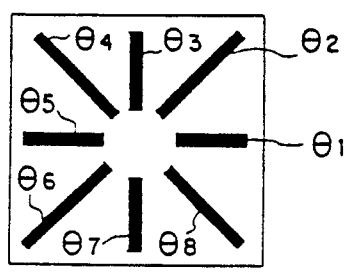
FIG. 13 is an explanatory view showing a displayed radial pattern in the aforementioned embodiment.
Figure 14:
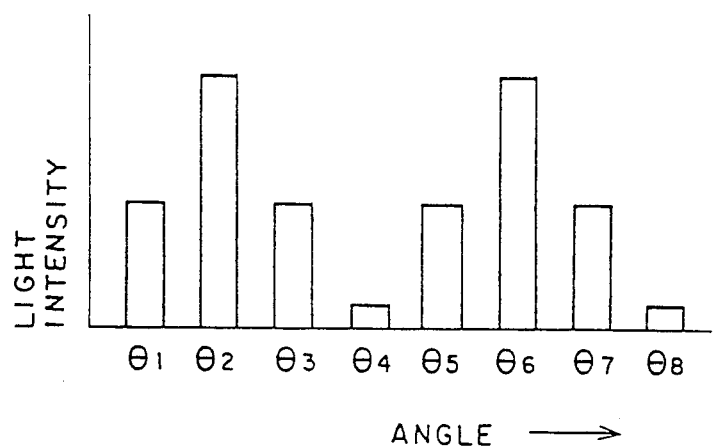
FIG. 14 is an explanatory view showing a polar coordinate developed result of said radial pattern.

The operation of the apparatus will be described below. FIG. 13 is an explanatory view showing a radial pattern displayed on the pattern display element 1a by the pattern generator 5c for automatically deciding the developing direction of the lattice pattern, and FIG. 14 is an explanatory view showing a polar coordinate developed result of the radial pattern. In the surface undulation inspection apparatus utilizing an optical lever effect by a principal ray, the pattern display element 1a as a patterning light source and a camera 3 for selectively focussing only the principal ray are arranged on one side and the other side, respectively, through the specimen to be inspected 2 so that an undulation is detected from a deviation of the lattice pattern picked up by the camera 3. On the other hand, in a case where the worked flaw remains on the surface of the specimen to be inspected 2, the visibility of the picked-up pattern sometimes is lowered dependent on the worked flaw and the direction of the pattern to render inspection difficult. Because of this, in the apparatus in Embodiment 6 shown in FIG. 12, the pattern generator 5c first generates a radial pattern as shown in FIG. 13, and an image of the principal ray of the pattern display element 1a which displays the radial pattern is picked up by the camera 3 through the specimen to be inspected 2. At this time, the image data taken from the camera 3 is subjected to polar coordinate development from the center of the image by the coordinate conversion circuit 17 and enters as data as shown in FIG. 14 into the angle detection circuit 18. The angle detection circuit 18 detects that the angles indicative of the maximum amplitude are $\theta_2$ and $\theta_6$ from the data shown in FIG. 14, and the angle data $\theta_2$ and $\theta_6$ are outputted to the pattern generator 5c. The pattern generator 5c controls the output in order to display the lattice developed to the angle at which the visibility of the image picked up pattern with respect to the specimen to be inspected 2 is maximum on the basis of the angle data $\theta_2$ and $\theta_6$. As the result, a stable picked-up pattern can be obtained, and an undulation is detected by the signal processor 10. It is expected that standard data of the finally developed lattice pattern is inputted for reference into the signal processor 10 to thereby facilitate the processing by the signal processor 10. In this case, the structure of apparatus comprises a combination of the Embodiments 4, 5 shown in FIGS. 8 and 11 and the Embodiment 6. Modes of embodiment of various inspection apparatuses caused by a difference in the way of combining the modes of embodiments are not beyond the claims of the present invention.

Embodiment 7

Figure 15:
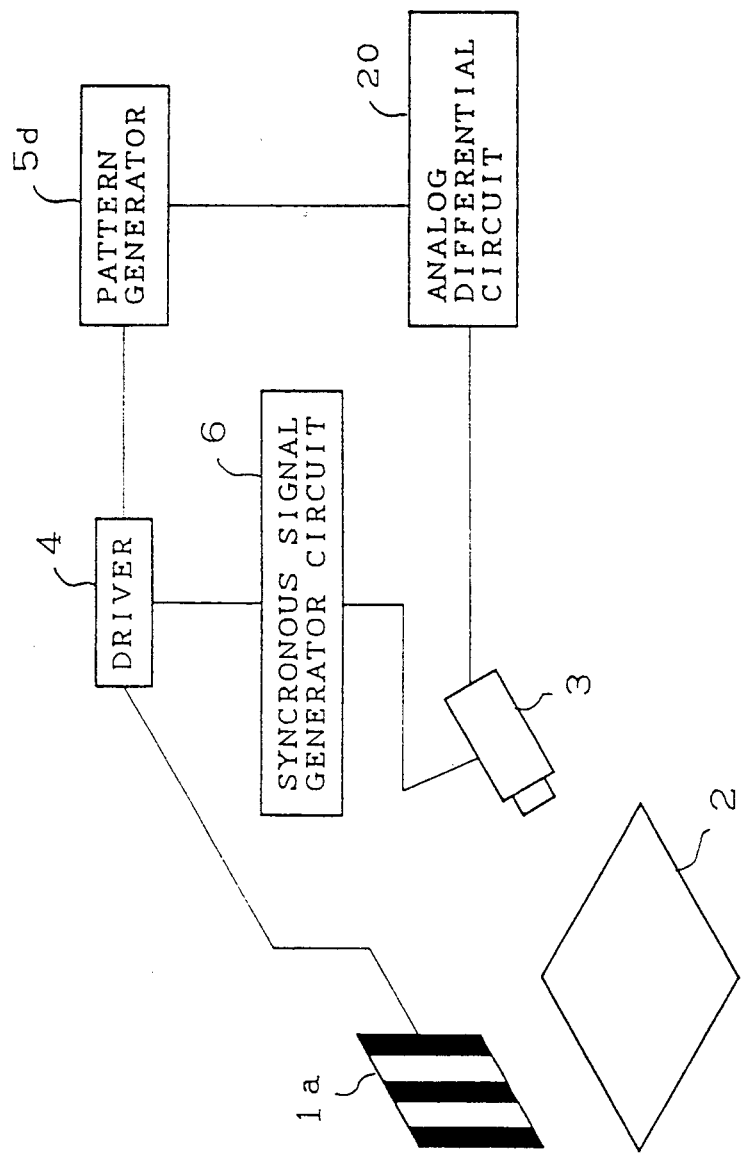
FIG. 15 is a structural view showing a surface undulation inspection apparatus according to a seventh embodiment of this invention.

Embodiment 7 of this invention will be described below with reference to the drawings. FIG. 15 is a structural view showing a surface undulation inspection apparatus for detecting an extremely small undulation defect so that it is embedded in a lattice pattern, in which the same parts as those shown in FIG. 12 are indicated by the same numerals. In FIG. 15, numeral 5d denotes a pattern generator different from those indicated by numerals 5, 5a to 5c shown in FIGS. 7, 8, 11 or 12 in that a display pattern is generated indicative of a regular change in intensity in an analog manner. Numeral 20 denotes an analog differential circuit for calculating a differential between an image data taken from the camera 3 and an output waveform of the pattern generator 5d to detect an abnormality.

Figure 16:
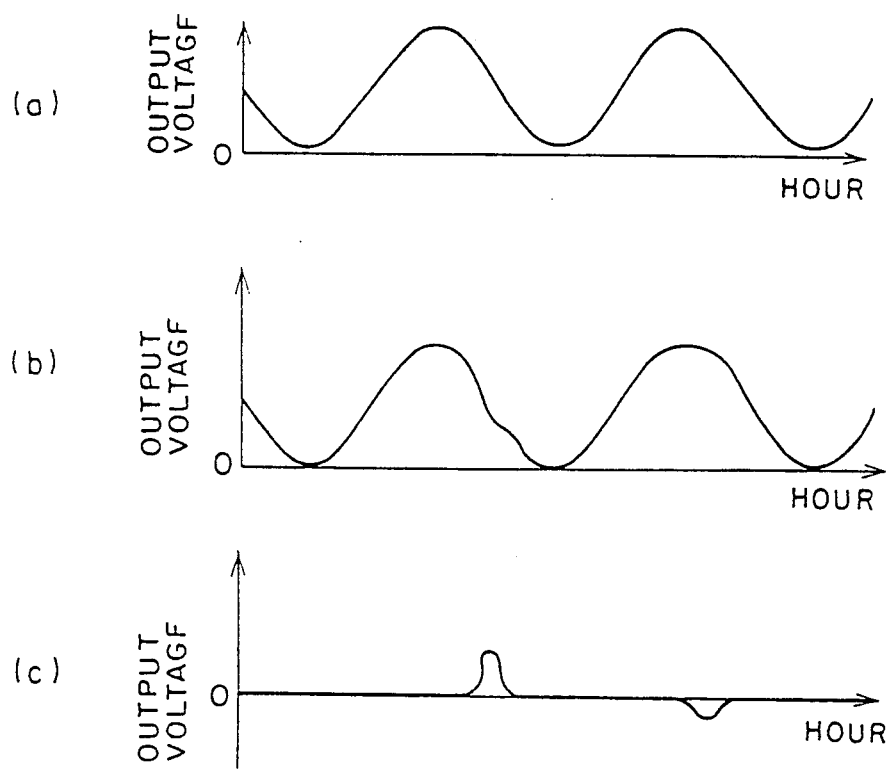
FIG. 16 is a waveform showing working voltages of various parts in the aforementioned embodiment.

The operation of the apparatus will be described below. FIGS. 16(a), 16(b) and 16(c) are waveforms showing output voltages. FIG. 16(a) shows an output waveform of the pattern generator 5d, FIG. 16(b) shows an output waveform of the camera 3, and FIG. 16(c) shows an output waveform of an analog differential circuit. In the surface undulation inspection apparatus utilizing an optical lever effect by a principal ray, the pattern display element 1a as a patterning light source and the camera 3 for selectively focussing only the principal ray are arranged on one side and the other side, respectively, through the specimen to be inspected 2, and an undulation is detected from a deviation of a lattice pattern picked up by the camera 3. On the other hand, when an undulation defect to be detected becomes extremely small, a change caused by the undulation becomes embedded into the pattern so that a change in shape of a pattern does not occur. Therefore, in the apparatus of Embodiment 7 shown in FIG. 15, the pattern generator 5d first generates a display pattern indicative of a regular change in intensity in an analog manner as shown in FIG. 16(a), which is displayed on the pattern display element 1a. An output of the camera 3 which has picked up the image of the principal ray of the light source pattern shows the same waveform as that shown in FIG. 16(a) in a case where no undulation defect is present on the surface of the specimen to be inspected 2. In a case where an undulation defect occurs on the surface of the specimen to be inspected 2, a delicate deviation of waveform as shown in FIG. 16(b) is represented according to experimental confirmation. Accordingly, a fine undulation as an analog amount of change as shown in FIG. 16(c) can be detected by taking a difference between the analog pattern generator 5d and the output voltage of the camera 3 by the analog differential circuit 20. The signal processing for detecting an abnormality from a change in output of the analog differential circuit 20 as shown in FIG. 16(c) can be realized within the range of the existing technology. Various modes of carrying out the inspection apparatus according to a device of the signal processing are not beyond the scope of claims of the present invention.

As described above, according to a first aspect of this invention, a patterning light source is opposed to a pin hole with a specimen to be inspected interposed therebetween, and the patterning light source is subjected to pin hole image-picking up through the specimen to be inspected whereby the ray passing through the specimen to be inspected can be specified as an optical principal ray to generate an optical lever effect, only the corresponding principal ray indicates an abnormality even with respect to a local surface undulation on the surface of the specimen, and the defect can be stressed and the defective part can be specified. Further, there are practical effects such that for detection of a pattern, a camera element such as a normal CCD is used, and a movement of a photoelectric element is not necessary.

According to a second aspect of this invention, an image pickup lens for focussing a patterning light source through a specimen to be inspected is disposed and only the principal ray among rays passing through the image pickup lens is selected at the pin hole, and therefore, even if the patterning light source does not have a high brightness and even if a reflectance of the surface of the specimen to be inspected is low, an undulation defect can be detected. Further, the field of vision of inspection can be suitably set as the field of vision of lens if the size of the patterning light source is sufficiently taken.

According to a third aspect of this invention, a display pattern generated by a pattern generator is displayed on a pattern display element, which is used as the patterning light source. With this arrangement, it is possible to obtain a surface undulation inspection apparatus which can promote the standardization of a light source hardware of a fine undulation inspection apparatus by picking up an image of a principal ray and lower cost resulting therefrom.

According to a fourth aspect of this invention, feedback control is applied to a pattern generator by a deviation calculation circuit and a standard data generator. With this arrangement, it is possible to obtain a surface undulation inspection apparatus capable of detecting even an undulation defect of the surface of a specimen to be inspected having a three-dimensional shape.

According to a fifth aspect of this invention, feedback control is applied to a pattern generator by a pattern width coincidence decision circuit and a comparison data circuit. With this arrangement, it is possible to obtain a surface undulation inspection apparatus capable of deciding an optimum lattice condition with respect to a limit defect.

According to a sixth aspect of this invention, a radial pattern is first projected, and feedback control is applied to a pattern generator by a coordinate conversion circuit and an angle detection circuit. With this arrangement, it is possible to obtain a surface undulation inspection apparatus capable of automatically setting a lattice pattern in an optimum direction with respect to a specimen to be inspected having a worked flaw.

According to a seventh aspect of this invention, an intensity of a display pattern is regularly changed in an analog manner, and an abnormality is detected on the basis of a differential from the image pickup data. With this arrangement, it is possible to obtain a surface undulation inspection apparatus capable of detecting even an extremely small undulation.

What is claimed is:

1. A surface undulation inspection apparatus in which a patterning light source and a camera are arranged on opposite sides with respect to a specimen to be inspected, said camera selectively focussing only a principal ray adjusted in focal point to said patterning light source through said specimen to be inspected, said apparatus comprising:
    a pattern display element used as a patterning light source,
    a pattern generator operatively connected to said pattern display element for generating a display pattern displayed on said pattern display element,
    a driver connected between said pattern generator and said pattern display element for causing the display pattern generated by said pattern generator to be displayed onto said pattern display element,
    a synchronous signal generator circuit connected to said driver and a camera for synchronizing said driver with scanning of the camera,
    a deviation calculation circuit connected to the camera for counting the number of stripes of an image data taken from the camera and calculating a deviation from a reference stripe pattern width data, and
    a standard data generator circuit connected to said deviation calculation circuit for producing said stripe pattern width data corresponding to a counted value of said number of stripes output from said deviation calculation circuit and to feed it back to said deviation calculation circuit,
    said pattern generator having a function of generating a stripe-like display pattern and changing said display pattern generated so that a deviation output by said deviation calculation circuit is zero.

2. The surface undulation inspection apparatus according to claim 1, comprising
    a pattern width coincidence decision circuit connected to the camera for comparing coincidence between a stripe pattern width data of an image data taken from the camera and a reference pattern width data, and
    a comparison data circuit connected to said pattern width coincidence decision circuit and said pattern generator for producing a pattern width data corresponding to a display pattern generated by said pattern generator to output it to said pattern width coincidence decision circuit,
    said pattern generator having a function of generating a stripe-like display pattern and changing said display pattern generated so that the number of stripes is increased and the stripe pitch is reduced until the decision result of said pattern width coincidence decision circuit indicates inconsistency.

3. The surface undulation inspection apparatus according to claim 1, comprising
    a coordinate conversion circuit connected to the camera for developing polar coordinates of an image data taken from the camera from the center of an image, and
    an angle detection circuit connected to said angle detection circuit and said pattern generator for detecting an angle at which a polar coordinate data output from said coordinate conversion circuit indicates a largest amplitude from among amplitudes of the polar coordinates, said pattern generator having a function of generating a lattice stripe-like display pattern parallel with the decision of an angle at which said polar coordinate data detected by said angle detection circuit indicates the largest amplitude after a radial display pattern is first generated.

4. The surface undulation inspection apparatus according to claim 1, wherein said pattern generator generates a display pattern indicative of a change in intensity in an analog manner, comprising an analog differential circuit connected to the camera and said pattern generator for calculating a differential between image data taken from the camera and an output waveform of said pattern generator to detect an abnormality occurring in a subfringe region.

5. A surface undulation inspection apparatus according to claim 1, comprising:

a pin hole, said patterning light source and said pin hole being arranged on opposite sides with respect to a specimen to be inspected, said camera arranged on an opposite side of said pin hole than the specimen to be inspected to detect an image of said patterning light source formed via said pin hole, and an image pickup lens for adjusting a focal point of the patterning light source which passes rays through the specimen to be inspected disposed between said specimens to be inspected and said pin hole, said pin hole arranged to select only a principal ray among rays through said image pick up lens.

6. The surface undulation apparatus according to claim 5, wherein said pin hole has a diameter of less than 1 mm.

* * * * *